(12) United States Patent
O'Connor et al.

(10) Patent No.: US 11,484,644 B2
(45) Date of Patent: *Nov. 1, 2022

(54) STERILE FLUID PATHWAY CONNECTION TO DRUG CONTAINERS FOR DRUG DELIVERY PUMPS

(71) Applicant: UNL Holdings LLC, New York, NY (US)

(72) Inventors: Sean M. O'Connor, West Chester, PA (US); Ian B. Hanson, Wayne, PA (US); Paul F. Bente, IV, Wayne, PA (US); Rajan Ramaswamy, San Diego, CA (US); Daniel S. Codd, Escondido, CA (US); Scott W. Beaver, San Marcos, CA (US); Kevin Bokelman, San Diego, CA (US); John C. Love, San Diego, CA (US)

(73) Assignee: UNL HOLDINGS LLC

( * ) Notice: Subject to any disclaimer, the term of this patent is extended or adjusted under 35 U.S.C. 154(b) by 388 days.

This patent is subject to a terminal disclaimer.

(21) Appl. No.: 16/532,402

(22) Filed: Aug. 5, 2019

(65) Prior Publication Data

US 2019/0358394 A1    Nov. 28, 2019

Related U.S. Application Data

(63) Continuation of application No. 15/651,807, filed on Jul. 17, 2017, now Pat. No. 10,369,274, which is a
(Continued)

(51) Int. Cl.
*A61M 5/142*    (2006.01)
*A61M 5/145*    (2006.01)
(Continued)

(52) U.S. Cl.
CPC ...... *A61M 5/14248* (2013.01); *A61M 5/1452* (2013.01); *A61M 5/162* (2013.01);
(Continued)

(58) Field of Classification Search
CPC ............ A61M 5/14248; A61M 5/1452; A61M 5/162; A61M 5/16813; A61M 5/16877; A61M 2005/1581
See application file for complete search history.

(56) References Cited

U.S. PATENT DOCUMENTS 3,336,924 A    8/1967 Sarnoff et al.
3,401,692 A    9/1968 Harris, Jr.
(Continued)

FOREIGN PATENT DOCUMENTS

CN    101557847 A    10/2009
CN    101631585 A    1/2010
(Continued)

OTHER PUBLICATIONS

Preliminary Amendment and Application Data Sheet Filed in National Phase of WO 2011/090956 A2 (U.S. Appl. No. 13/521,181) (dated Jul. 9, 2012), entitled "Cartridge Interface Assembly."
(Continued)

*Primary Examiner* — Theodore J Stigell

(57) ABSTRACT

A user-initiated fluid pathway connection includes: a connection hub, a piercing member, a sterile sleeve, and a drug container having a cap, a pierceable seal, a barrel, and a plunger seal, wherein the piercing member is initially retained within the sterile sleeve between the connection hub and the pierceable seal of the drug container. The connection hub may include an internal aperture within the connection hub which functions as a flow restrictor and wherein a piercing member is connected to one end of the internal aperture and a fluid conduit is connected to another end of
(Continued)

the internal aperture. A drug delivery pump with integrated sterility maintenance features includes a housing, upon which an activation mechanism, an insertion mechanism, a fluid pathway connection as described above, a power and control system, and a drive mechanism connected to a drug container are mounted. Methods of assembly and operation are also provided.

16 Claims, 6 Drawing Sheets

Related U.S. Application Data continuation of application No. 13/612,203, filed on Sep. 12, 2012, now Pat. No. 9,707,337.

(60) Provisional application No. 61/534,059, filed on Sep. 13, 2011.

(51) Int. Cl.
 *A61M 5/168* (2006.01)
 *A61M 5/162* (2006.01)
 *A61M 5/158* (2006.01)

(52) U.S. Cl.
 CPC .... *A61M 5/16813* (2013.01); *A61M 5/16877* (2013.01); *A61M 2005/1581* (2013.01)

(56) References Cited

U.S. PATENT DOCUMENTS

| | | | |
|---|---|---|---|
| 3,413,974 A | 12/1968 | Cohen | |
| 3,940,003 A | 2/1976 | Larson | |
| 4,004,586 A | 1/1977 | Christensen et al. | |
| 4,048,997 A | 9/1977 | Raghavachari et al. | |
| 4,565,543 A | 1/1986 | Bekkering et al. | |
| 4,673,400 A | 6/1987 | Martin | |
| 4,685,903 A | 8/1987 | Cable et al. | |
| 4,755,173 A | 7/1988 | Konopka et al. | |
| 4,840,620 A | 6/1989 | Kobayashi et al. | |
| 5,147,311 A | 9/1992 | Pickhard | |
| 5,167,816 A | 12/1992 | Kruger et al. | |
| 5,616,132 A | 4/1997 | Newman | |
| 5,766,147 A | 6/1998 | Sancoff et al. | |
| 5,795,339 A | 8/1998 | Erskine | |
| 5,851,197 A | 12/1998 | Marano et al. | |
| 5,858,001 A | 1/1999 | Tsals et al. | |
| 6,030,363 A * | 2/2000 | Kriesel | A61M 5/1454 604/132 |
| 6,248,093 B1 | 6/2001 | Moberg | |
| 6,368,314 B1 | 4/2002 | Kipfer et al. | |
| 6,699,218 B2 | 3/2004 | Flaherty et al. | |
| 7,063,684 B2 | 6/2006 | Moberg | |
| 7,250,037 B2 | 7/2007 | Shermer et al. | |
| D564,087 S | 3/2008 | Yodfat et al. | |
| D585,543 S | 1/2009 | Yodfat et al. | |
| 7,479,135 B2 | 1/2009 | Richter et al. | |
| D586,463 S | 2/2009 | Evans et al. | |
| 7,611,503 B2 | 11/2009 | Spohn et al. | |
| 7,780,636 B2 | 8/2010 | Radmer et al. | |
| 7,803,134 B2 | 9/2010 | Sharifi et al. | |
| D629,503 S | 12/2010 | Caffey et al. | |
| 7,846,132 B2 | 12/2010 | Gravesen et al. | |
| 7,879,010 B2 | 2/2011 | Hunn et al. | |
| 7,905,859 B2 | 3/2011 | Bynum et al. | |
| 7,927,306 B2 | 4/2011 | Cross et al. | |
| 7,967,795 B1 | 6/2011 | Cabiri | |
| 8,029,472 B2 | 10/2011 | Leinsing et al. | |
| 8,048,031 B2 | 11/2011 | Shaw et al. | |
| 8,152,771 B2 | 4/2012 | Mogensen et al. | |
| 8,157,769 B2 | 4/2012 | Cabiri | |
| 8,162,892 B2 | 4/2012 | Mogensen et al. | |
| 8,167,844 B2 | 5/2012 | Dillard, III | |
| 8,187,232 B2 | 5/2012 | Chong et al. | |
| 8,192,394 B2 | 6/2012 | Estes et al. | |
| D669,165 S | 10/2012 | Estes et al. | |
| 8,409,145 B2 | 4/2013 | Raymond et al. | |
| D684,685 S | 6/2013 | Schneider et al. | |
| D684,686 S | 6/2013 | Cronenberg | |
| D685,083 S | 6/2013 | Schneider et al. | |
| 8,591,465 B2 | 11/2013 | Hommann | |
| D709,183 S | 7/2014 | Kemlein | |
| 8,795,234 B2 | 8/2014 | Kadamus et al. | |
| 8,939,935 B2 | 1/2015 | O'Connor et al. | |
| D723,157 S | 2/2015 | Clemente et al. | |
| 9,005,169 B2 | 4/2015 | Gravesen et al. | |
| D745,142 S | 12/2015 | O'Connor et al. | |
| D752,442 S | 3/2016 | O'Donahue | |
| D768,288 S | 10/2016 | O'Connor et al. | |
| 9,463,280 B2 | 10/2016 | Cabiri | |
| 9,511,189 B2 | 12/2016 | O'Connor et al. | |
| D791,306 S | 7/2017 | Clemente et al. | |
| 9,707,335 B2 | 7/2017 | Agard et al. | |
| 9,707,337 B2 * | 7/2017 | O'Connor | A61M 5/1452 |
| 9,802,030 B2 | 10/2017 | Clemente et al. | |
| 10,369,274 B2 * | 8/2019 | O'Connor | A61M 5/16813 |
| 11,033,676 B2 | 6/2021 | Dechelette | |
| 2003/0199816 A1 | 10/2003 | Ramming | |
| 2004/0092878 A1 | 5/2004 | Flaherty | |
| 2006/0200073 A1 * | 9/2006 | Radmer | A61M 5/14248 604/93.01 |
| 2007/0010789 A1 | 1/2007 | Peter et al. | |
| 2007/0179444 A1 | 8/2007 | Causey et al. | |
| 2008/0132842 A1 | 6/2008 | Flaherty | |
| 2008/0269683 A1 | 10/2008 | Bikovsky | |
| 2008/0269687 A1 | 10/2008 | Chong et al. | |
| 2008/0269713 A1 | 10/2008 | Kavazov | |
| 2009/0124979 A1 | 5/2009 | Raymond et al. | |
| 2009/0204077 A1 | 8/2009 | Hasted et al. | |
| 2009/0240240 A1 | 9/2009 | Hines et al. | |
| 2011/0098652 A1 | 4/2011 | Hasted et al. | |
| 2011/0160678 A1 | 6/2011 | Chong et al. | |
| 2011/0166509 A1 | 7/2011 | Gross et al. | |
| 2011/0270188 A1 | 11/2011 | Caffey et al. | |
| 2012/0035546 A1 | 2/2012 | Cabiri | |
| 2012/0096953 A1 | 4/2012 | Bente, IV et al. | |
| 2012/0123354 A1 | 5/2012 | Woehr | |
| 2012/0211946 A1 | 8/2012 | Halili et al. | |
| 2013/0060196 A1 | 3/2013 | O'Connor et al. | |
| 2013/0060233 A1 | 3/2013 | O'Connor et al. | |
| 2013/0066274 A1 | 3/2013 | O'Connor et al. | |
| 2013/0131595 A1 | 5/2013 | Ekman et al. | |
| 2014/0200510 A1 | 7/2014 | Agard et al. | |
| 2014/0213975 A1 | 7/2014 | Clemente et al. | |
| 2015/0141920 A1 | 5/2015 | O'Connor et al. | |
| 2015/0359965 A1 | 12/2015 | O'Connor et al. | |
| 2016/0199583 A1 | 7/2016 | Tan-Malecki et al. | |
| 2017/0080149 A1 | 3/2017 | O'Connor et al. | |
| 2017/0281859 A1 | 10/2017 | Agard et al. | |
| 2018/0008769 A1 | 1/2018 | O'Connor et al. | |
| 2019/0022306 A1 | 1/2019 | Gibson et al. | |
| 2019/0167895 A1 | 6/2019 | Dechelette | |

FOREIGN PATENT DOCUMENTS

| | | |
|---|---|---|
| EP | 589328 A2 | 3/1994 |
| EP | 1219283 A2 | 7/2002 |
| EP | 1 495 775 A1 | 1/2005 |
| EP | 1702635 A2 | 9/2006 |
| EP | 1341569 B1 | 1/2007 |
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2269559 A2 | 1/2011 |
| EP | 2379134 A1 | 10/2011 |
| EP | 2429612 A1 | 3/2012 |
| EP | 2433663 A1 | 3/2012 |
| JP | S59-500600 A | 8/1983 |
| JP | 09-502116 A | 3/1997 |
| JP | 2000-189494 A | 7/2000 |
| JP | 2002-507459 A | 3/2002 |

(56) References Cited

FOREIGN PATENT DOCUMENTS

| | | |
|---|---|---|
| JP | 2002-524217 A | 8/2002 |
| JP | 2003-527159 A | 9/2003 |
| JP | 2004-195227 A | 7/2004 |
| JP | 2004-528939 A | 9/2004 |
| JP | 2010-501211 A | 1/2010 |
| JP | 2010-501281 A | 1/2010 |
| JP | 2010-528810 A | 8/2010 |
| JP | 2010-531196 A | 9/2010 |
| JP | 2010-538751 A | 12/2010 |
| JP | 2011-045537 A | 3/2011 |
| JP | 2011-511689 A | 4/2011 |
| WO | WO 95/19194 A1 | 7/1995 |
| WO | WO 96/40327 A1 | 12/1996 |
| WO | WO 99/30768 A1 | 6/1999 |
| WO | WO 99/48546 A1 | 9/1999 |
| WO | WO 00/15292 A2 | 3/2000 |
| WO | WO 01/30424 A1 | 5/2001 |
| WO | WO 2003/024504 A2 | 3/2003 |
| WO | WO 03/103763 A1 | 12/2003 |
| WO | WO 2004/035116 A1 | 4/2004 |
| WO | WO 2004/062714 A1 | 7/2004 |
| WO | WO 2005/002492 * | 1/2005 |
| WO | WO 2005/002492 A1 | 1/2005 |
| WO | WO 2005/037350 A2 | 4/2005 |
| WO | WO 2005/044344 A1 | 5/2005 |
| WO | WO 2006/129196 A1 | 12/2006 |
| WO | WO 2008/024808 A2 | 2/2008 |
| WO | WO 2008/105954 A2 | 9/2008 |
| WO | WO 2008/133702 A1 | 11/2008 |
| WO | WO 2008/153460 A1 | 12/2008 |
| WO | WO 2009/044401 A2 | 4/2009 |
| WO | WO 2009/101145 A1 | 8/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | WO 2010/112377 A1 | 10/2010 |
| WO | WO 2010/132196 A1 | 11/2010 |
| WO | WO 2010/139672 A1 | 12/2010 |
| WO | WO 2011/006652 A1 | 1/2011 |
| WO | WO 2011/014514 A1 | 2/2011 |
| WO | WO 2011/046950 A1 | 4/2011 |
| WO | WO 2011/090956 A1 | 7/2011 |
| WO | WO 2011/121023 A1 | 10/2011 |
| WO | WO 2012/032411 A2 | 3/2012 |
| WO | WO 2012/131044 A1 | 10/2012 |
| WO | WO 2013/033467 A2 | 3/2013 |
| WO | WO 2013/040032 A1 | 3/2013 |
| WO | WO 2013/134279 A1 | 9/2013 |
| WO | WO 2013/156224 A1 | 10/2013 |
| WO | WO 2014/011879 A2 | 1/2014 |
| WO | WO 2016/048878 A1 | 3/2016 |
| WO | WO 2016/049532 A1 | 3/2016 |
| WO | WO 2016/141082 A1 | 9/2016 |
| WO | WO 2018/029520 A1 | 2/2018 |

OTHER PUBLICATIONS

U.S. Food and Drug Administration, "Infusion Pump Improvement Initiative," Apr. 2010, 6 pp.

Meng et al., "MEMS-enabled implantable drug infusion pumps for laboratory animal research. preclinical, and clinical applications," *Adv. Drug. Deliv. Rev.,* 64(14): 1628-1638 (Nov. 2012).

International Search Report and Written Opinion for Int'l Application No. PCT/US2012/054861, titled: Sterile Fluid Pathway Connection To Drug Containers For Drug Delivery Pumps, dated Feb. 18, 2013.

International Preliminary Report on Patentability for Int'l Application No. PCT/US2012/054861, titled: Sterile Fluid Pathway Connection To Drug Containers For Drug Delivery Pumps, dated Mar. 18, 2014.

Non-Final Office Action for U.S. Appl. No. 13/612,203, dated Jan. 2, 2015.

Final Office Action for U.S. Appl. No. 13/612,203, dated Jun. 30, 2015.

Advisory Action for U.S. Appl. No. 13/612,203, dated Jul. 28, 2015.

Non-Final Office Action for U.S. Appl. No. 13/612,203, dated Jan. 13, 2016.

Final Office Action for U.S. Appl. No. 13/612,203, dated Jul. 21, 2016.

First Notice of Allowance for U.S. Appl. No. 13/612,203, dated Dec. 6, 2016.

Second Notice of Allowance for U.S. Appl. No. 13/612,203, dated Mar. 13, 2017.

Non-Final Office Action for U.S. Application No. 15/651,807, dated Jul. 17, 2018.

Final Office Action for U.S. Appl. No. 15/651,807, dated Dec. 20, 2018.

Notice of Allowance for U.S. Appl. No. 15/651,807, dated Apr. 1, 2019.

* cited by examiner

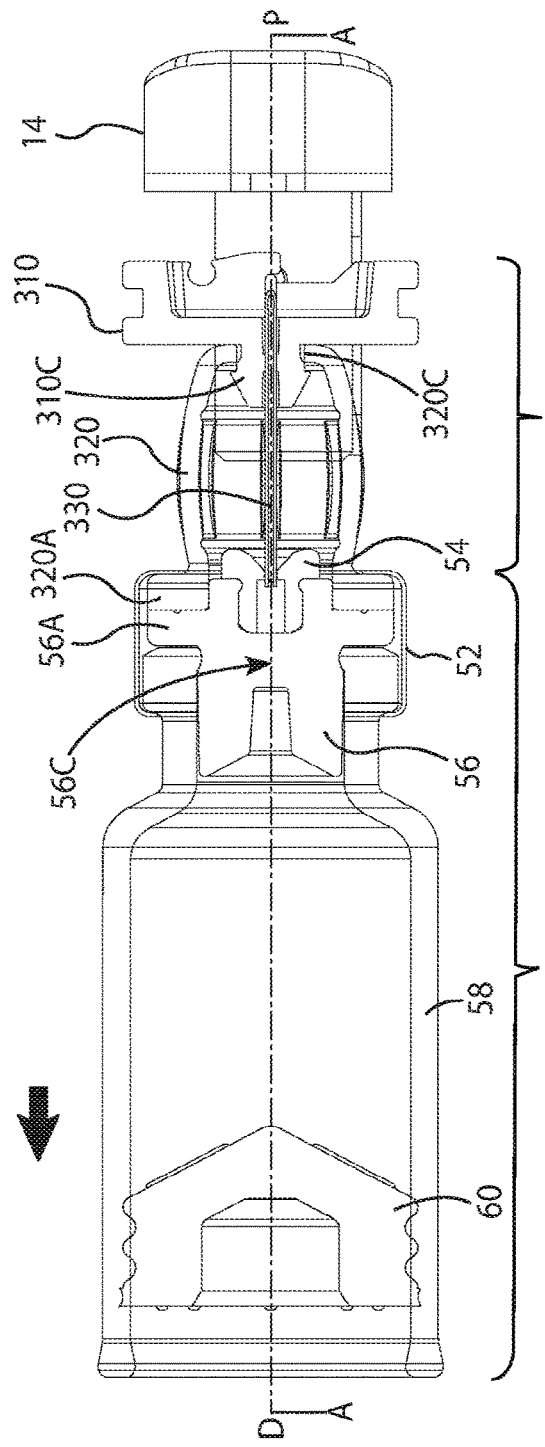
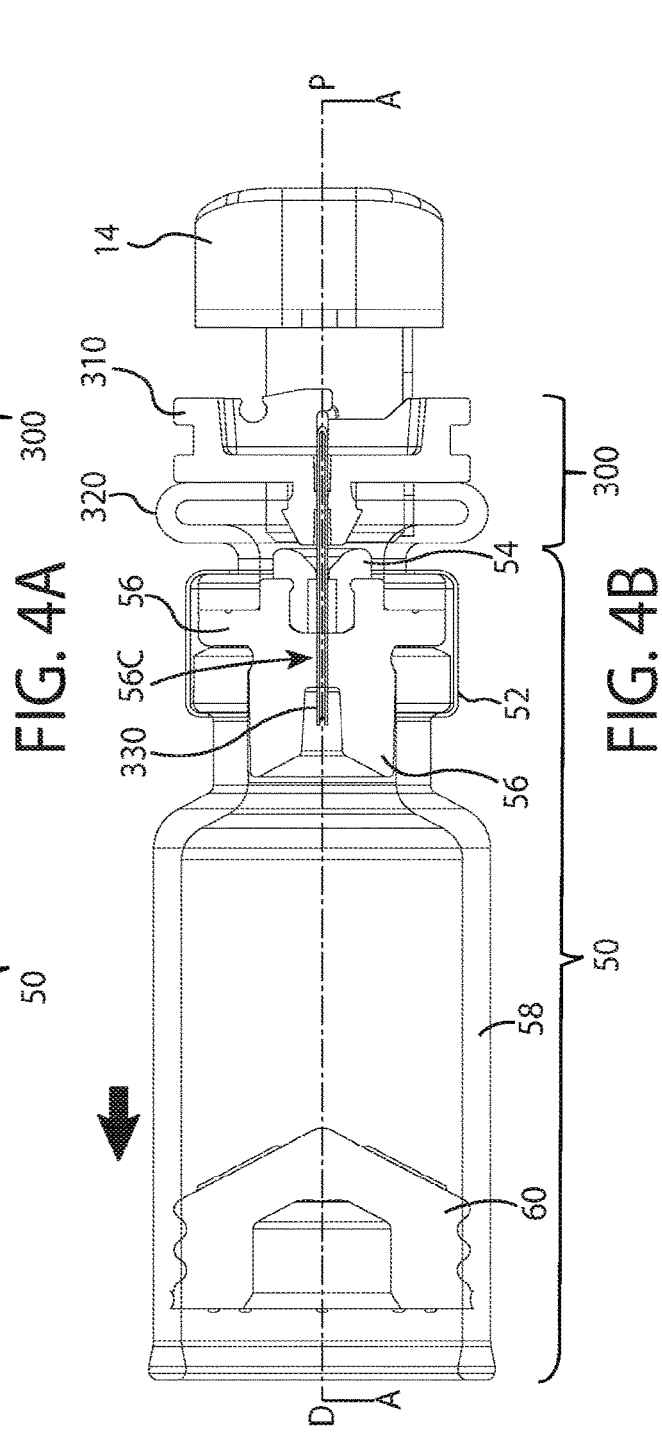
FIG. 4A
FIG. 4B

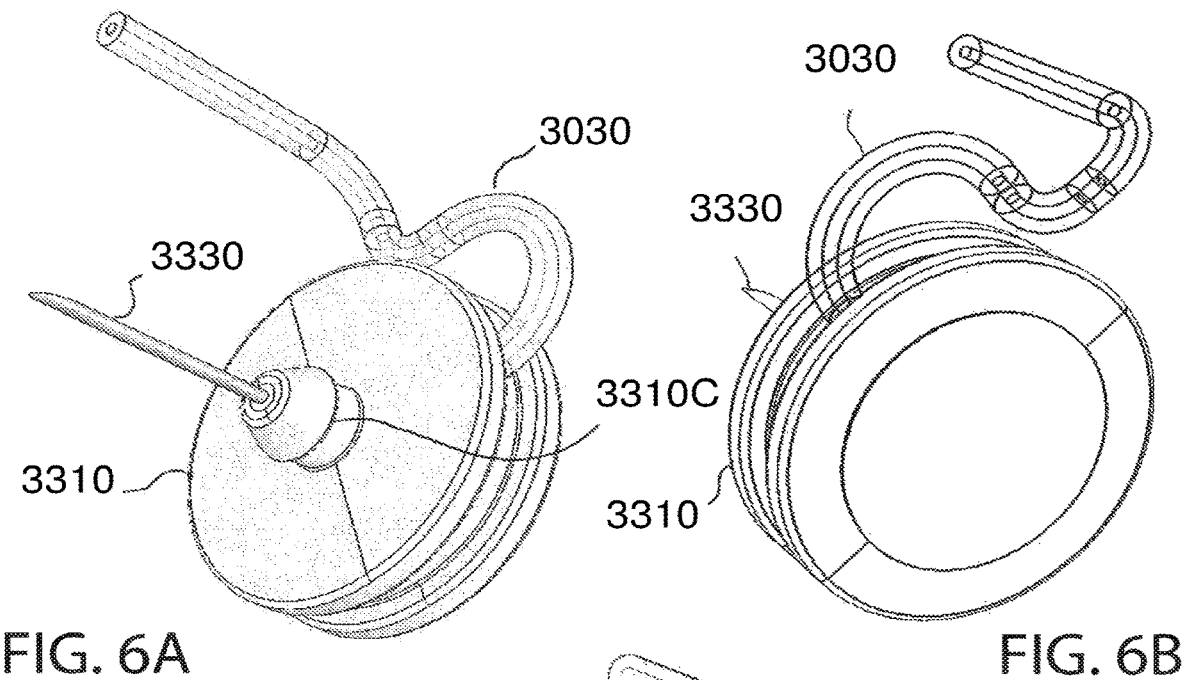
FIG. 6A
FIG. 6B
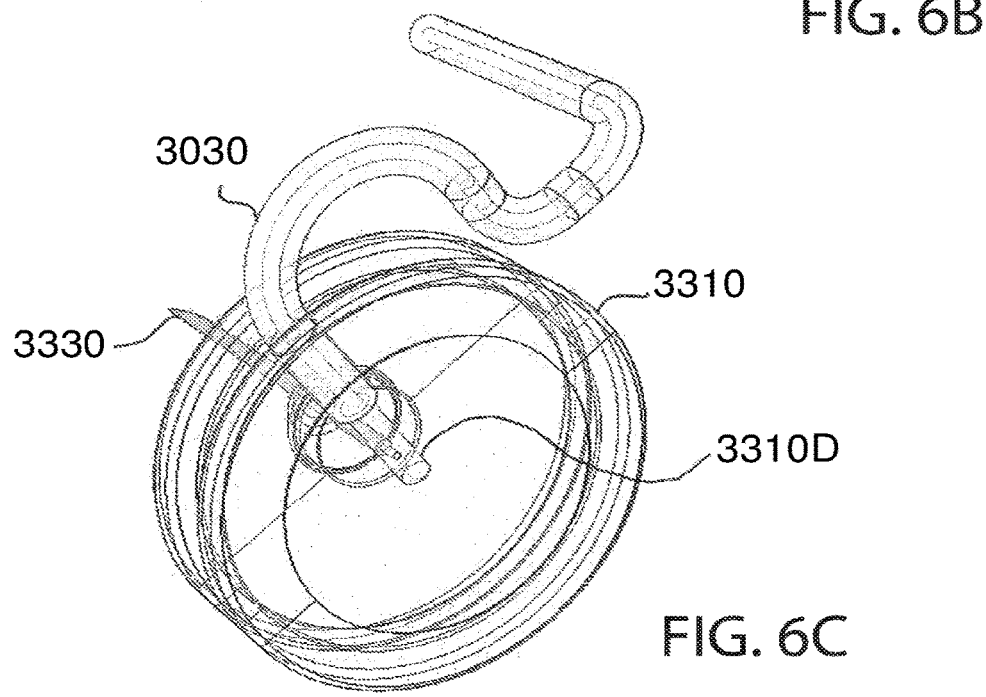
FIG. 6C

STERILE FLUID PATHWAY CONNECTION TO DRUG CONTAINERS FOR DRUG DELIVERY PUMPS

CROSS-REFERENCE TO RELATED APPLICATIONS

This application is a continuation of U.S. patent application Ser. No. 15/651,807, filed Jul. 17, 2017, which is a continuation of U.S. patent application Ser. No. 13/612,203, filed Sep. 12, 2012, which issued as U.S. Pat. No. 9,707,337, and which claims priority to U.S. Provisional Patent Appl. No. 61/534,059, filed Sep. 13, 2011. The entire teachings of the above application(s) are incorporated herein by reference.

FIELD

THIS INVENTION relates to drug delivery pumps. More particularly, this invention relates to user-initiated sterile fluid pathway connections to drug containers, drug delivery pumps which utilize these connections, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides container connections which are user-initiated and which maintain the sterility of the fluid pathway, and drug delivery pumps which incorporate such sterile fluid pathway connections to drug containers, the methods of operating such devices, and the methods of assembling such devices. The fluid pathway connections of the present invention provide integrated safety features which ensure the sterility of the fluid pathway before, during, and after drug delivery. In one aspect, the fluid pathway remains disconnected from the drug container until the connection and the device are initiated by the user. In a second aspect, the fluid pathway maintains the sterility of the piercing member prior to connection with the drug container within a sterile sleeve that is collapsible or compressible to enable connection upon activation by the user. Upon activation by the user, the piercing member of the fluid pathway connection is caused to pierce a pierceable seal of the drug container to connect the fluid pathway and enable fluid flow through the fluid pathway for drug delivery into the body of the user. Accordingly, the novel devices of the present invention alleviate one or more of the problems associated with prior art devices, such as those referred to above.

In a first embodiment, the present invention provides a user-initiated fluid pathway connection. The fluid pathway connection includes: a connection hub, a piercing member, a sterile sleeve, and a drug container having a cap, a pierceable seal, a barrel, and a plunger seal, wherein the piercing member is initially retained within the sterile sleeve between the connection hub and the pierceable seal of the drug container. The drug container may contain a drug fluid for delivery, upon initiation by the user, through the fluid pathway connection to the body of the user. The pierceable seal includes a seal barrier that may be penetrated, upon user initiation, by the piercing member. In at least one embodiment, the piercing member is initially within the pierceable seal and in contact with, or adjacent to, the seal barrier. Such a configuration may minimize the distance the fluid pathway connection must be translated to enable connection of the fluid path. The fluid pathway connection may optionally include a connection mount attached to the pierceable seal.

The sterile sleeve of the fluid pathway connection is compressible or collapsible, or otherwise deformable from its initial configuration. In at least one embodiment, the sterile sleeve is a pre-formed aspect of the pierceable seal such that the two are a unified component. The sterile sleeve may be connected to the connection hub by engagement between hub connectors of the sterile sleeve and corresponding sleeve connectors of the connection hub. In one embodiment, the piercing member passes through the connection hub and connects to a fluid conduit. One or more optional flow restrictors may be utilized. Displacement of an activation mechanism by a user causes displacement of the connection hub to cause the piercing member to penetrate the pierceable seal.

In another embodiment, the present invention provides a flow restricting fluid pathway connection having a piercing member and a sterile sleeve, wherein the piercing member is initially retained within the sterile sleeve, a drug container having a cap, a pierceable seal, a barrel, and a plunger seal, and a connection hub having an internal aperture therein to modify the flow of a drug fluid passing there-through. The pierceable seal has a seal barrier that may be penetrated, upon user initiation, by the piercing member. In a preferred embodiment, the piercing member is initially within the pierceable seal and in contact with, or adjacent to, the seal barrier. The sterile sleeve is compressible or collapsible, or otherwise deformable from its initial configuration. In a preferred embodiment, the sterile sleeve is a pre-formed aspect of the pierceable seal. The sterile sleeve is connected to the connection hub by engagement between hub connectors of the sterile sleeve and corresponding sleeve connectors of the connection hub. The piercing member connects to one end of an internal aperture within the connection hub and a fluid conduit connects to another end of the internal aperture. In a preferred embodiment, the internal aperture may be utilized to function as a flow restrictor. Displacement of an activation mechanism by a user causes displacement of the connection hub to cause the piercing member to penetrate the pierceable seal.

In yet another embodiment, the present invention provides a drug delivery pump with integrated sterility maintenance features having a housing and an assembly platform, upon which an activation mechanism, an insertion mechanism, a fluid pathway connection, a power and control system, and a drive mechanism having a drug container may be mounted, said fluid pathway connection including a connection hub, a piercing member, a sterile sleeve, wherein the drug container has a cap, a pierceable seal, a barrel, and a plunger seal, and wherein the piercing member is initially retained within the sterile sleeve between the connection hub and the pierceable seal of the drug container. The drug container contains a drug fluid for delivery into the body of a user. The pierceable seal has a seal barrier that may be penetrated, upon user initiation, by the piercing member. In at least one embodiment, the piercing member is initially within the pierceable seal and in contact with, or adjacent to, the seal barrier. Such a configuration may minimize the distance the fluid pathway connection must be translated to enable connection of the fluid path. Displacement of an activation mechanism by a user causes displacement of the connection hub to cause the piercing member to penetrate the pierceable seal.

The novel embodiments of the present invention provide user-initiated fluid pathway connections to drug containers, and drug pumps which utilize such connections which are capable of maintaining the sterility of the fluid pathway before, during, and after operation of the device, and which enable active safety controls for the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 4A shows a cross-sectional view of the fluid pathway connection attached to a drug container, as shown in FIG. 2B, prior to user activation;

FIG. 4B shows a cross-sectional view of the fluid pathway connection attached to a drug container, as shown in FIG. 2B, with the fluid pathway connected by the user;

FIG. 6A shows an isometric view, from the distal perspective, of a connection hub, according to another embodiment of the present invention;

FIG. 6B shows an isometric view, from the proximal perspective, of the connection hub shown in FIG. 6A;

FIG. 6C shows a transparent view of the connection hub shown in FIG. 6B.

DETAILED DESCRIPTION

Figure 1A:
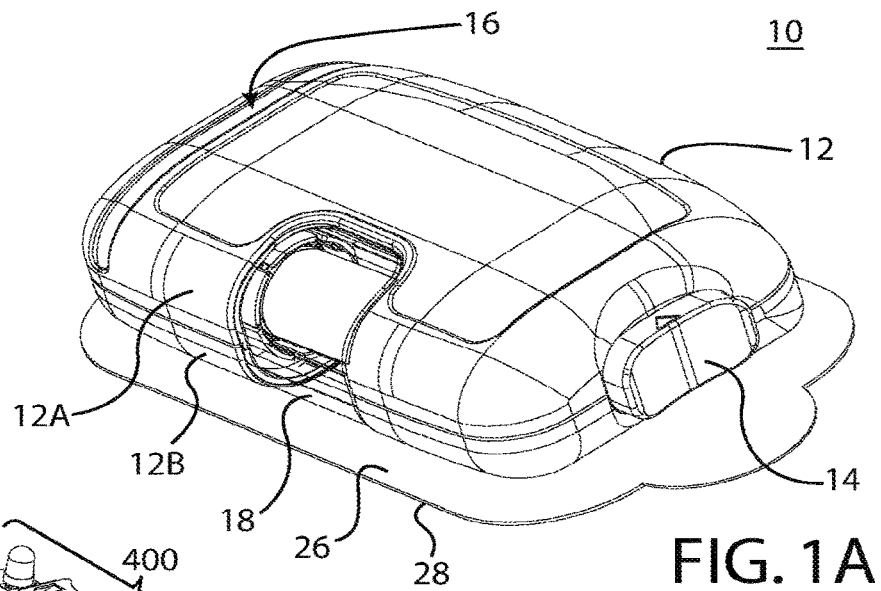
FIG. 1A shows an isometric view of a drug delivery pump having a sterile fluid pathway connect, according to one embodiment of the present invention.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be resoftened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the pumps. According to various aspects and embodiments described herein, reference is made to a "biasing member", which may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide container connections which are user-initiated and which maintain the sterility of the fluid pathway, and drug delivery pumps which incorporate such sterile fluid pathway connections to drug containers. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, fluid pathway connections, and their respective components are described further herein with reference to the accompanying figures.

Figure 1B:
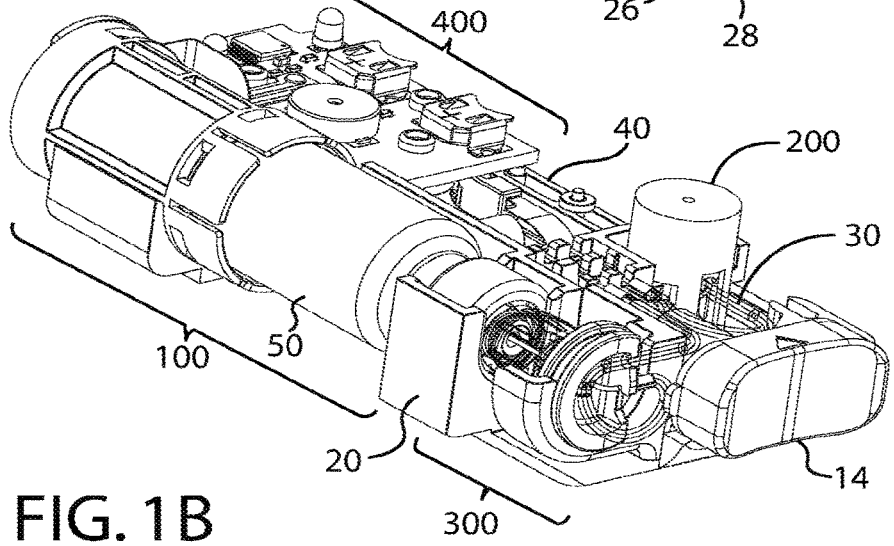
FIG. 1B shows an isometric view of the interior components of the drug delivery pump shown in FIG. 1A.
Figure 1C:
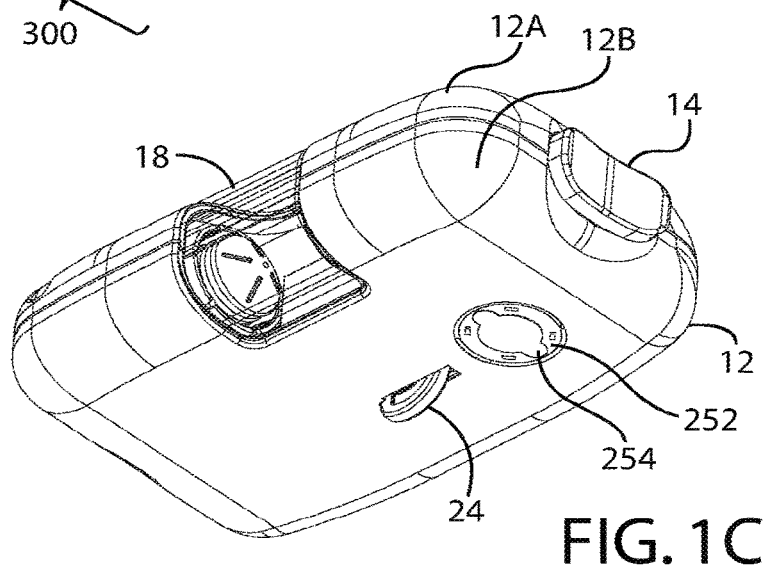
FIG. 1C shows an isometric view of the bottom of the drug delivery pump shown in FIG. 1A.

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing sub-components which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400.

In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

Drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump.

For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Insertion Mechanism

A number of insertion mechanisms may be utilized within the drug pumps of the present invention. In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least one embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to use-stage by lockout pin(s) which are initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

Drive Mechanism

A number of drive mechanisms may be utilized to force fluid from a drug container for delivery into the body of a user. In one such embodiment, the drive mechanism 100 includes a drive housing, a status switch interconnect, and a drug container having a cap, a pierceable seal, a barrel, and a plunger seal. The drug container may contain a drug fluid, within the barrel between the pierceable seal and the plunger seal, for delivery through the insertion mechanism and drug pump into the body of the user. The seals described herein may be comprised of a number of materials but are, in a preferred embodiment, comprised of one or more elastomers or rubbers. The drive mechanism may further include a connection mount to guide the insertion of the piercing member of the fluid pathway connection into the barrel 58 of the drug container. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the body of the user.

In one particular embodiment, the drive mechanism 100 employs one or more compression springs as the biasing member(s). Upon activation of the drug pump by the user, the power and control system 400 may be actuated to directly or indirectly release the compression spring(s) from an energized state. Upon release, the compression spring(s) may bear against and act upon the plunger seal to force the fluid drug out of the drug container. The fluid pathway connection 300 may be connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

The components of the drive mechanism 100, upon activation, may be used to drive axial translation in the distal direction of the plunger seal of the drug container. Optionally, the drive mechanism 100 may include one or more compliance features which enable additional axial translation of the plunger seal to, for example, ensure that substantially the entire drug dose has been delivered to the user and make sure that the feedback contact mechanisms have connected. Additionally or alternatively, the plunger seal, itself, may have some compressibility permitting a compliance push of drug fluid from the drug container.

The drive mechanism 100 may similarly include one or more status indication mechanisms, such as interconnects and contacts, to measure and communicate the status of the drive mechanism before, during, and after operation of the drive mechanism and the device to the user. Furthermore, the drive mechanism 100 may include one or more safety mechanisms, such as premature activation prevention mechanisms, to enhance the safety and usability of the mechanism and the device. Further details related to the drive mechanism 100 are provided herein with reference to other components of the drug pump.

Fluid Pathway Connection

Figure 2A:
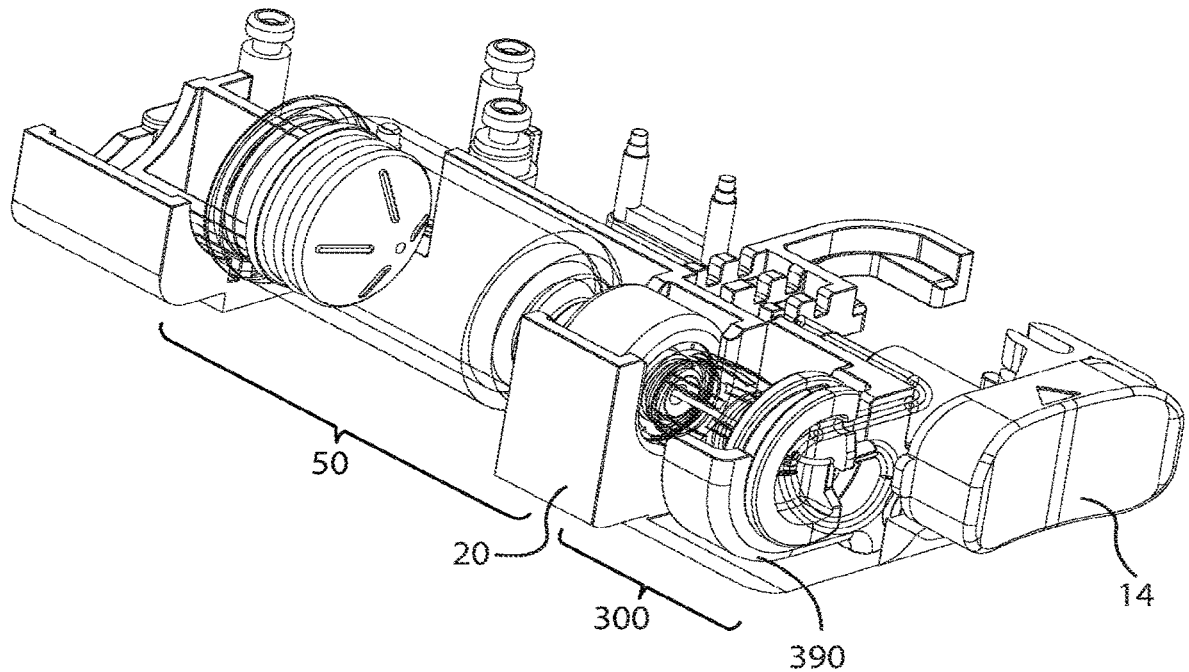
FIG. 2A shows an isometric view of the user-initiated fluid pathway connections to drug containers, according to one embodiment of the present invention.
Figure 2B:
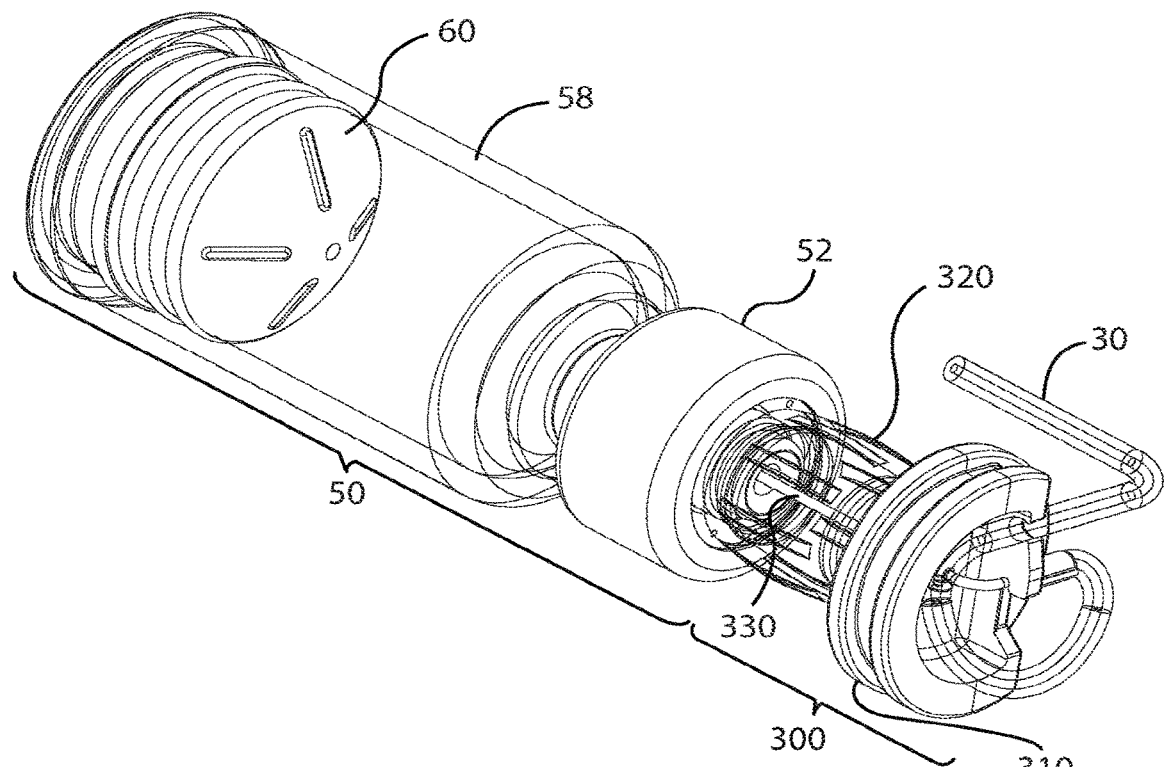
FIG. 2B shows an isometric view of the fluid pathway connection shown in FIG. 2A attached to a drug container.

The novel embodiments of the present invention provide user-initiated fluid pathway connections to drug containers, and drug pumps which utilize such connections which are capable of maintaining the sterility of the fluid pathway before, during, and after operation of the device, and which enable active safety controls for the device. In one embodiment, the fluid pathway connection 300 includes a sterile fluid conduit 30, a piercing member 330, a connection hub 310, and a sterile sleeve 320, as shown in FIGS. 2A and 2B. The fluid pathway connection may, optionally, further include one or more flow restrictors. Upon proper activation of the device 10 by the user, the fluid pathway connection 300 is connected to the drug container 50, thereby enabling fluid flow from the drug container (as may be forced by the drive mechanism 100), through the fluid pathway connection 300, the fluid conduit 30, the insertion mechanism 200 and into the body of the user. Such connection between the fluid pathway connection 300 and the drug container 50 may be facilitated by a piercing member 330, such as a needle, penetrating a pierceable seal 56 (shown in FIGS. 3A, 3B, 4A, and 4B) of the drug container 50. The sterility of this connection may be maintained by performing the connection within a flexible sterile sleeve 320. Upon substantially simultaneous activation of the insertion mechanism 200, the fluid pathway between drug container 50 and insertion mechanism 200 is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In a preferred embodiment, this connection is enabled by the user depressing the activation mechanism and, thereby, driving the piercing member through the pierceable seal. Because the fluid pathway connection is not connected to the drug container until activation by the user, fluid flow from the drug container is prevented until desired by the user. This provides an important safety feature to the user while also maintaining the container integrity of the drug container and sterility of the fluid pathway. In such an embodiment, a collapsible or compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation of the device and connection between the fluid pathway connection and the drug container.

As shown in FIG. 2A, the fluid pathway connection 300 may be attached to a drug container 50 and mounted, by a number of known methods, either fixedly or removably to an assembly platform 20 or housing of the drug pump. The assembly platform may be a separate component from the housing, or may be a unified component of the housing such a pre-formed mounting aspect on the interior surfaces of the housing. In one embodiment, the drug container 50 may be mounted, connected, or otherwise attached to a fixed aspect of the assembly platform 20 or housing, while the fluid pathway connection 300 is mounted, connected, or otherwise attached to a movable guide 390 that is capable of being translated upon user translation of the activation mechanism 14. In an alternative embodiment, this configuration can be reversed such that the drug container 50 is attached to a movable guide 390 and the fluid pathway connection 300 is attached to a fixed aspect of the assembly platform 20 or housing. In either configuration, the sterility of the fluid pathway is maintained, the pathway for fluid flow is not connected until desired by the user, and user-initiated activation causes the connection of the drug container and the fluid pathway connection. While the former configuration is preferred, the latter configuration may be desired in certain embodiments such as, for example, those which utilize cartridge-style drug containers. User translation or similar displacement of the activation mechanism 14 causes displacement, either directly or indirectly, of the guide 390 to enable a connection between the fluid pathway connection and the drug container. Such displacement of the guide 390 may optionally be assisted, for example to reduce the activation force needed by the user acting upon the activation mechanism 14, by a number of different biasing members including compression springs, extension springs, elastic bands, or the like.

FIG. 2B shows the fluid pathway connection 300 and the drug container 50 apart from the housing, assembly platform, and other components of the drug pump. As stated above, drug container 50 may include barrel 58 having a plunger seal 60 at one end and a cap 52 at another end. The fluid pathway connection 300 may be mounted, connected, or otherwise attached to the drug container 50 at the cap 52. At least in an initial configuration, a piercing member 330 is maintained within a sterile sleeve 320 with a distal end adjacent to, or contacting, a pierceable seal of the drug container 50. The piercing member 330 may be a number of cannulas or conduits, such as rigid needles, and may be comprised of a number of materials, such as steel. In at least one embodiment, the piercing member 330 is a rigid steel needle. The sterile sleeve 320 is a compressible or collapsible membrane positioned between the drug container 50 and the connection hub 310 and provides a sterile environment within which the piercing member 330 may reside. The sterile sleeve 320 may be comprised of a number of materials which are compressible or collapsible, but preferably is an elastomeric membrane. The sterile sleeve 320 may be a number of different shapes or configurations, including cones, pyramids, ellipsoids, ovoids, spheres, octahedron (diamond-shaped), and the like, which are capable of being compressed, collapsed, or otherwise deformed to permit two adjacent components to become closer together while maintaining sterility of an interior environment within the sleeve. Similarly, the sterile sleeve 320 may have one or more aspects, such as longitudinal (i.e., axial) and/or latitudinal (i.e., radial) groove striations, ridges, valleys, accordion folds, and the like, which promote compressibility or collapsibility. Such aspects may be positioned equidistant or non-equidistant, and in a myriad of configurations including along the inner surface, the outer surface, or both surfaces of the sterile sleeve. FIG. 2B shows an embodiment having longitudinal grooves which are equidistant along the circumferential exterior surface of the sterile sleeve 320.

Figures 3A, 3B:
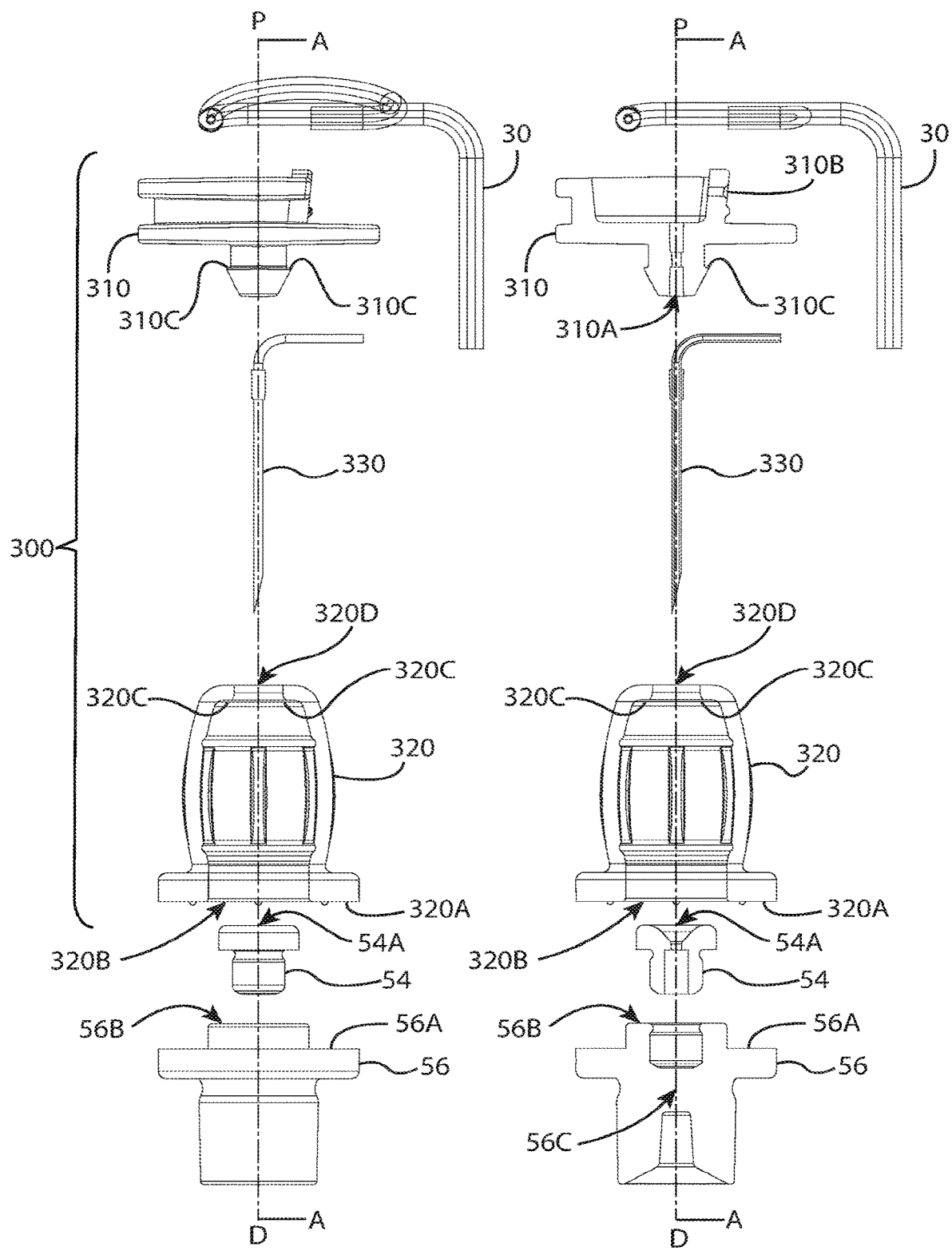
FIG. 3A shows an exploded view of the fluid pathway connection, exploded along a longitudinal axis "A," according to at least one embodiment of the present invention.
FIG. 3B shows a cross-sectional exploded view of the fluid pathway connection shown in FIG. 3A.

The piercing member 330 is maintained in a sterile environment within the sterile sleeve 320. This sterile environment is maintained between the connection hub 310 and the cap 52 of the drug container 50. FIG. 3A shows an exploded view of the arrangement of the components of the fluid pathway connection, according to at least one embodiment of the present invention, while FIG. 3B shows a cross-sectional exploded view. These figures include certain components of the drug container, specifically the pierceable seal 56 and the optional connection mount 54, as they relate to the connection of the fluid pathway connection 300. As shown, a sleeve interface surface 320A of the sterile sleeve 320 is caused to contact a seal interface surface 56A of pierceable seal 56 upon assembly. These corresponding interface surfaces may be retained in position and/or connection by cap 52, as shown in FIGS. 4A and 4B, such that a distal end of the sterile sleeve 320 may be held fixed within the cap 52 while the remainder of the sterile sleeve 320 is outside the cap 52. When utilized, the optional connection mount 54 may reside within a seal recess 56B of the pierceable seal 56, and within the sterile interior environment of the sterile sleeve 320. Alternatively, the pierceable seal 56 and the sterile sleeve 320 may be two aspects of a single pre-formed component (i.e., a unified component having two or more functions). In such a configuration, the cap 52 may similarly be utilized to hold the components in place at a proximal end of the drug container 50 (and attached to the proximal end of the barrel 58). In either of these embodiments, the sterile sleeve 320 may have a container connection opening 320B at a distal end through which the piercing member 330 may translate to pierce the pierceable seal 56 and enable the fluid flow connection with the drug container 50. Alternatively, the connection opening 320B may be a closed surface and function as a pierceable sealing membrane between the fluid pathway and the drug container. However, in at least a preferred embodiment of the present invention, pierceable seal 56 has a seal barrier 56C that would be pierced to open the drug container to the fluid pathway. In an initial position, the distal end of the piercing member 330 may reside adjacent to, or in contact with, the seal barrier 56C of the pierceable seal 56 to, for example, minimize the distance of translation of the fluid pathway connection 300 to pierce the pierceable seal 56 and open the drug container to the fluid pathway. In one particular embodiment, the distal end of the piercing member 330 may reside at least partially within the seal barrier 56C of the pierceable seal 56, yet not fully passing there-through until activation of the device by the user. When an optional connection mount 54 is utilized, for example to ensure axial piercing of the pierceable seal 56, the piercing member 330 may pass through a piercing member recess 54A of the connection mount 54.

Figure 5A:
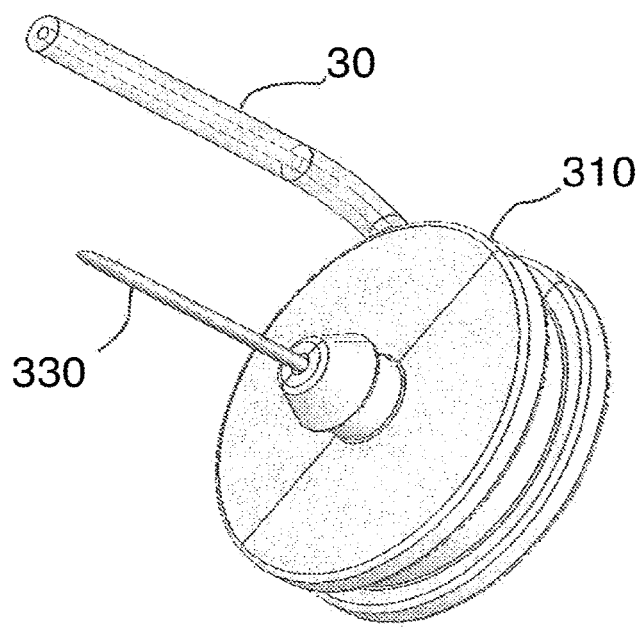
FIG. 5A shows an isometric view, from the distal perspective, of a connection hub, according to one embodiment of the present invention.
Figure 5B:
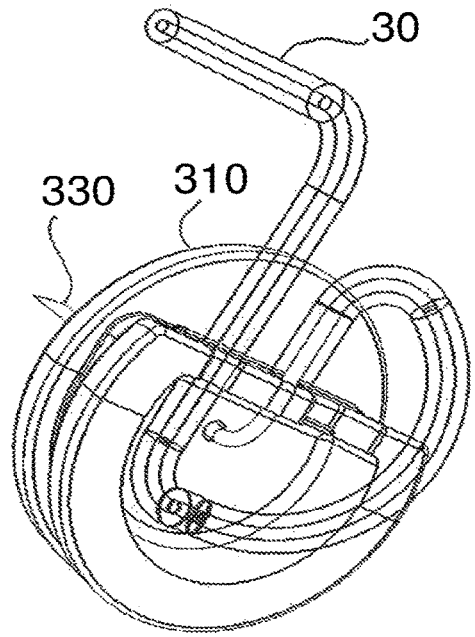
FIG. 5B shows an isometric view, from the proximal perspective, of the connection hub shown in FIG. 5A.
Figure 5C:
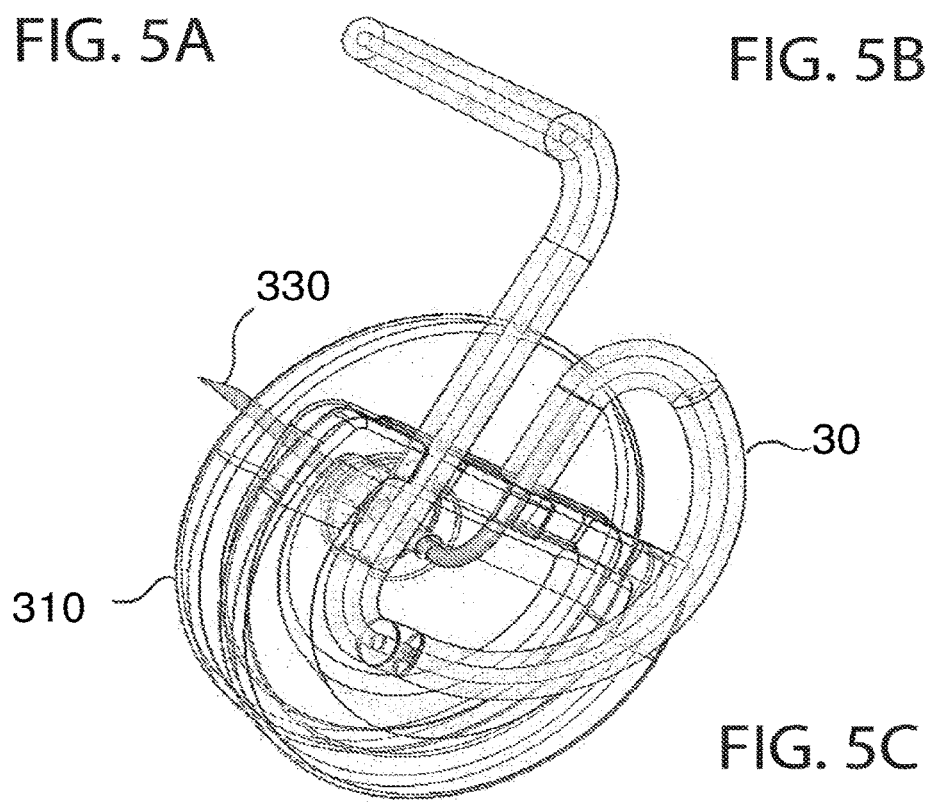
FIG. 5C shows a transparent view of the connection hub shown in FIG. 5B.

The sterile sleeve 320 is connected at a proximal end to a connection hub 310. In one embodiment, this connection is facilitated by engagement between hub connectors 320C of sterile sleeve 320 and corresponding sleeve connectors 310C of connection hub 310. This engagement can be a snap-fit, interference fit, screw fit, or a number of other connective linkages. The piercing member 330 passes through the connection hub 310 and is held in place at the piercing member connection aperture 310A. As described further below, in one embodiment the connection hub 310 is configured to accept a bent piercing member 330 such that the piercing member passes through and is held in place at both the piercing member connection aperture 310A and the conduit connection aperture 310B. The fluid conduit 30 is connected to the proximal end of the piercing member 330 at the conduit connection aperture 310B. As would be readily appreciated by an ordinary skilled artisan, a number of glues or adhesives, or other connection methods such as snap-fit, interference fit, screw fit, fusion joining, welding, ultrasonic welding, and the like may optionally be utilized to engage one or more of the components described herein. FIGS. 5A-5C, show a connection hub 310 according to one embodiment of the present invention, with a fluid conduit 30 and a piercing member 330 attached. FIGS. 5A and 5B show that the piercing member 330 may pass through the connection hub 310. FIG. 5C provides a transparent view of the connection hub 310, in an embodiment having a bent piercing member 330 which connects to the fluid conduit 30 as described above.

One or more optional flow restrictors may be utilized within the configurations of the fluid pathway connection described herein. For example, a flow restrictor may be utilized at the connection between the piercing member 330 and the fluid conduit 30. The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof.

In one embodiment of the present invention, the connection hub itself may be utilized as part of the fluid path and may, optionally, function as a flow restrictor. FIGS. 6A and 6B show such an embodiment, where connection hub 3310 has a piercing member 3330 and a fluid conduit 3030 connected at opposite ends of an internal aperture 3310D of the connection hub 3310 (visible in the transparent view shown in FIG. 6C). Accordingly, the internal aperture 3310D functions as part of the fluid path and may be utilized to restrict or otherwise modify the flow of fluid from the drug container 50 to the insertion mechanism 200 for delivery of the drug fluid to the body of the user. For example, the internal aperture 3310D may have a smaller diameter than the fluid conduit 30 to restrict the fluid flow through the fluid pathway connection 300. Additionally or alternatively, the internal aperture 3310D may be configured to extend the length of the fluid path to prolong the time it takes for drug to flow from the drug container to the user. For example, while the embodiment shown in FIG. 6C shows a straight, short distance internal aperture 3310D, the internal aperture may be a circuitous or tortuous path within the connection hub which extends the fluid pathway and/or provides further flow restriction to the system. By utilizing one or more non-reactive materials and/or non-reactive polymers to form the connection hub 3310, the container integrity and sterility of the fluid path may be maintained.

Referring now to FIGS. 4A and 4B, upon displacement by the user of the activation mechanism 14 (in the direction of the solid arrow) the piercing member 330 is caused to penetrate the pierceable seal 56 (through the seal barrier 56C) to open the fluid path from the drug container 50 to the fluid pathway connection 300. As described above, because the piercing member 330 is maintained in a sterile environment within the sterile sleeve 320, the sterility of the fluid path is not compromised. The compressible or collapsible sterile sleeve 320 is deformed to permit the translation or displacement of the fluid pathway connection 300 upon user initiation. FIG. 4A shows an embodiment of the present invention which utilizes a sterile sleeve 320 and a pierceable seal 56 as separate components, attached to the proximal end of a barrel 58 of the drug container 50 by a cap 52. As described above, however, sterile sleeve 320 and pierceable seal 56 may be a unified component that provides two or more functions. An optional connection mount 54 is also shown to guide the piercing member 330 upon activation. In this embodiment, the sterile sleeve 320 is shown to deform radially as it is compressed in the axial direction. However, in other embodiments the sterile sleeve 320 may be caused to collapse upon itself in the axial direction such as in, for example, an accordion-style sterile sleeve 320. By keeping the fluid path disconnected until use by the user, the sterility of the fluid pathway and the drug container are maintained. This novel configuration also provides an additional safety feature to the user which prevents drug flow until desired, and actively initiated, by the user.

As described herein, the fluid pathway connection, and specifically a sterile sleeve of the fluid pathway connection, may be connected to the cap and/or pierceable seal of the drug container upon user-initiated activation of the device. A fluid conduit may be connected at one end to the fluid pathway connection and at another end to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of sterile pathway connection 300 or drug pump 10 are contemplated while remaining within the breadth and scope of the present invention. For example, upper or lower housings may optionally contain one or more transparent or translucent windows 18, as shown in FIG. 1A, to enable the user to view the operation of the drug pump 10 or verify that drug dose has completed. Additionally, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C). Furthermore, as described above, a number of flow restrictors may be optionally utilized to modify the flow of fluid within the fluid pathway connection.

Similarly, one or more of the components of fluid pathway connection 300 and drug pump 10 may be modified while remaining functionally within the breadth and scope of the present invention. For example, as described above, while the housing of drug pump 10 is shown as two separate components upper housing 12A and lower housing 12B, these components may be a single unified component. Similarly, while sterile sleeve 320 is shown as a separate component from pierceable seal 56, it may be a unified component pre-formed as part of pierceable seal. As discussed above, a glue, adhesive, or other known materials or methods may be utilized to affix one or more components of the fluid pathway connection and/or drug pump to each other. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the fluid pathway connections and drug pumps disclosed herein provide an efficient and easily-operated system for automated drug delivery from a drug container. The novel devices of the present invention provide container connections which are user-initiated and which maintain the sterility of the fluid pathway, and drug delivery pumps which incorporate such sterile fluid pathway connections to drug containers. Such devices are safe and easy to use, and are aesthetically and ergonomically appealing for self-administering patients. The devices described herein incorporate features which make activation, operation, and lock-out of the device simple for even untrained users. Because the fluid path is disconnected until drug delivery is desired by the user, the sterility of the fluid pathway connection, the drug container, the drug fluid, and the device as a whole is maintained. These aspects of the present invention provide highly desirable storage, transportation, and safety advantages to the user. Furthermore, the novel configurations of the fluid pathway connections and drug pumps of the present invention maintain the sterility of the fluid path through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, housing and other components of the pump drug may readily be configured to accept and operate connection hub 310, connection hub 3310, or a number of other variations of the components described herein.

Assembly and/or manufacturing of fluid pathway connection 300, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The fluid pathway connection may be assembled in a number of methodologies. In one method of assembly, the drug container 50 may be assembled and filled with a fluid for delivery to the user. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 to guide the insertion of the piercing member of the fluid pathway connection into the barrel 58 of the drug container 50. The drug container 50 may then be mounted to a distal end of drive housing 130. The sterile sleeve 320 may be connected to the pierceable seal 56 and held in fixed contact by the cap 52, as described above. The connection hub 310, fluid conduit 30, and piercing member 330 may be assembled together and then attached to the proximal end of the sterile sleeve 320 by engagement between hub connectors 320C of sterile sleeve 320 and corresponding sleeve connectors 310C of connection hub 310, as shown in FIG. 4A. The drive mechanism 100 may be attached to the distal end of the drug container 50. The insertion mechanism 200 may be assembled and attached to the other end of the fluid conduit 30. This entire sub-assembly, including drive mechanism 100, drug container 50, fluid pathway connection 300, fluid conduit 30, and insertion mechanism 200 may be sterilized, as described above, before assembly into the drug pump 10. Certain components of this sub-assembly may be mounted to the assembly platform 20 or directly to the interior of the housing 12, while other components are mounted to the guide 390 for activation by the user.

Manufacturing of a drug pump includes the step of attaching both the fluid pathway connection and chug container, either separately or as a combined component, to an assembly platform or housing of the drug pump. The method of manufacturing further includes attachment of the drive mechanism, drug container, and insertion mechanism to the assembly platform or housing. The additional components of the drug pump, as described above, including the power and control system, the activation mechanism, and the control aim may be attached, preformed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; displacing a guide to translate a fluid pathway connection; and actuating a power and control system to activate a drive control mechanism to chive fluid drug flow through the drug pump, wherein translating the fluid pathway connection causes a piercing member to penetrate a pierceable seal thereby opening a fluid path from a drug container to the fluid pathway connection. The method may further include the step of engaging an optional on-body sensor prior to activating the activation mechanism. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user. The method of operation of the insertion mechanism and the drug pump may be better appreciated with reference to FIGS. 4A-4B, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A method of assembling a fluid pathway connection, the method comprising:
   fixedly engaging a pierceable seal between a cap and a barrel of a drug container;
   connecting one end of a sterile sleeve to the pierceable seal, the connecting including disposing the one end of the sterile sleeve to be held in fixed contact with the pierceable seal, the fixed contact of the one end of the sterile sleeve and the pierceable seal being retained by the cap;
   connecting an opposing end of the sterile sleeve to a connection hub including a piercing member, a distal end of the piercing member being disposed within the sterile sleeve between the connection hub and the pierceable seal of the drug container in an initial unactivated position, the sterile sleeve being compressible or collapsible and adapted to compress or collapse upon relative movement of the connection hub and the pierceable seal between the initial unactivated position and an activated position; and
   connecting a fluid conduit to be in fluid communication with a proximal end of the piercing member.

2. The method of claim 1, wherein connecting the opposing end of the sterile sleeve to the connection hub includes fixedly engaging a hub connector of the sterile sleeve and a corresponding sleeve connector of the connection hub.

3. The method of claim 1, wherein the distal end of the piercing member is disposed adjacent to a seal barrier of the pierceable seal in the initial unactivated position.

4. The method of claim 1, wherein the distal end of the piercing member is disposed in contact with a seal barrier of the pierceable seal in the initial unactivated position.

5. The method of claim 1, further comprising disposing a connection mount within a seal recess of the pierceable seal.

6. The method of claim 5, wherein the distal end of the piercing member is disposed within the connection mount in the initial unactivated position.

7. The method of claim 1, further comprising filling the barrel of the drug container with a fluid through an open distal end of the barrel and inserting a plunger seal through the distal end of the barrel.

8. The method of claim 1, wherein the connection hub, the piercing member, and the barrel are substantially coaxially disposed.

9. The method of claim 1, wherein connecting the fluid conduit to be in fluid communication with the proximal end of the piercing member includes connecting the fluid conduit to the proximal end of the piercing member at a conduit connection aperture of the connection hub.

10. The method of claim 1, wherein connecting the fluid conduit to be in fluid communication with the proximal end of the piercing member includes connecting the fluid conduit to one end of an internal aperture of the connection hub and connecting the proximal end of the piercing member to an opposing end of the internal aperture.

11. A method of manufacturing a drug pump comprising:
    assembling a fluid pathway connection according to claim 1;
    attaching an insertion mechanism to the fluid conduit;
    attaching a drive mechanism to the drug container; and
    disposing a power and control system, an activation mechanism, and the assembled fluid path pathway connection, insertion mechanism, and drive mechanism within a housing of the drug pump.

12. The method of claim 11, further comprising sterilizing the assembled fluid pathway connection and insertion mechanism prior to attaching the drive mechanism to the drug container.

13. The method of claim 11, further comprising sterilizing the assembled fluid pathway connection, insertion mechanism, and drive mechanism prior to disposing the power and control system, activation mechanism, and assembled fluid path pathway connection, insertion mechanism, and drive mechanism within the housing of the drug pump.

14. The method of claim 11, further comprising disposing the activation mechanism along an axis of the connection hub.

15. A method of assembling a fluid pathway connection, the method comprising:
 fixedly engaging a pierceable seal between a cap and a barrel of a drug container, the pierceable seal integrally formed with a sterile sleeve and disposed at one end of the sterile sleeve;
 connecting an opposing end of the sterile sleeve to a connection hub including a piercing member, a distal end of the piercing member being disposed within the sterile sleeve between the connection hub and the pierceable seal of the drug container in an initial unactivated position, the sterile sleeve being compressible or collapsible and adapted to compress or collapse upon relative movement of the connection hub and the pierceable seal between the initial unactivated position and an activated position; and
 connecting a fluid conduit to be in fluid communication with a proximal end of the piercing member.

16. A method of assembling a fluid pathway connection, the method comprising:
 fixedly engaging a pierceable seal between a cap and a barrel of a drug container;
 connecting one end of a sterile sleeve to the pierceable seal;
 disposing a connection mount within a seal recess of the pierceable seal, a distal end of a piercing member disposed within the connection mount in an initial unactivated position;
 connecting an opposing end of the sterile sleeve to a connection hub including the piercing member, the distal end of the piercing member being disposed within the sterile sleeve between the connection hub and the pierceable seal of the drug container in the initial unactivated position, the sterile sleeve being compressible or collapsible and adapted to compress or collapse upon relative movement of the connection hub and the pierceable seal between the initial unactivated position and an activated position; and
 connecting a fluid conduit to be in fluid communication with a proximal end of the piercing member.

* * * * *

UNITED STATES PATENT AND TRADEMARK OFFICE
CERTIFICATE OF CORRECTION

| | |
|---|---|
| PATENT NO. | : 11,484,644 B2 |
| APPLICATION NO. | : 16/532402 |
| DATED | : November 1, 2022 |
| INVENTOR(S) | : Sean M. O'Connor et al. |

It is certified that error appears in the above-identified patent and that said Letters Patent is hereby corrected as shown below:

On the Title Page

Item (72), Line 7, "Kevin Bokelman," should be -- Kevin L. Bokelman, --.

Signed and Sealed this
Twelfth Day of November, 2024

*Katherine Kelly Vidal*

Katherine Kelly Vidal
*Director of the United States Patent and Trademark Office*